(12) United States Patent
Cabias et al.

(10) Patent No.: US 8,742,193 B2
(45) Date of Patent: Jun. 3, 2014

(54) PROCESS FOR OLIGOMERIZATION OF LIGHT OLEFINS USING A CATALYST BASED ON AN AMORPHOUS MATERIAL WITH HIERARCHIZED AND ORGANIZED POROSITY

(75) Inventors: Amandine Cabias, Lyons (FR); Alexandra Chaumonnot, Lyons (FR); Laurent Simon, Villeurbanne (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 741 days.

(21) Appl. No.: 12/994,213

(22) PCT Filed: Apr. 28, 2009

(86) PCT No.: PCT/FR2009/000500
§ 371 (c)(1),
(2), (4) Date: Feb. 9, 2011

(87) PCT Pub. No.: WO2009/153420
PCT Pub. Date: Dec. 23, 2009

(65) Prior Publication Data
US 2011/0124936 A1    May 26, 2011

(30) Foreign Application Priority Data
May 28, 2008    (FR) .................. 08 02948

(51) Int. Cl.
*C07C 2/10*    (2006.01)
*C07C 2/12*    (2006.01)

(52) U.S. Cl.
USPC .......... 585/533; 585/502; 585/520; 585/530; 585/531; 585/532

(58) Field of Classification Search
USPC ............ 585/502, 520, 530, 531, 532, 533
See application file for complete search history.

(56) References Cited

U.S. PATENT DOCUMENTS

| | | | |
|---|---|---|---|
| 5,260,501 A * | 11/1993 | Bhore et al. ............. | 585/533 |
| 5,625,108 A * | 4/1997 | Perego et al. ............. | 585/520 |
| 6,585,952 B1 | 7/2003 | Pinnavaia et al. | |
| 6,746,659 B2 * | 6/2004 | Pinnavaia et al. .......... | 423/702 |
| 2005/0201920 A1 * | 9/2005 | Shan et al. ............... | 423/335 |
| 2006/0030477 A1 * | 2/2006 | Chaumonnot et al. ....... | 502/64 |
| 2006/0063955 A1 * | 3/2006 | Lacombe et al. ........... | 585/535 |
| 2006/0292054 A1 * | 12/2006 | Chaumonnot et al. ..... | 423/328.1 |
| 2009/0232720 A1 | 9/2009 | Chaumonnot et al. | |

FOREIGN PATENT DOCUMENTS

| | | |
|---|---|---|
| EP | 1627852 A1 | 2/2006 |
| EP | 1627853 A1 | 2/2006 |
| WO | 2006128989 A1 | 12/2006 |

OTHER PUBLICATIONS

"Standard Test Sieves" in CRC Handbook of Chemistry and Physics, 94th ed., 2014 Internet Version, D. R. Lide, editor, accessed Aug. 20, 2013.*
Barker, et al., "Petroleum" in Kirk-Othmer Encyclopedia of Chemical Technology, John Wiley & Sons, 2001, available on-line May 13, 2005.*
World IP Organization. "International Search Report and Written Opinion." PCT/FR2009/000500, Applicant: IFP, Mailed: Oct. 2, 2009.
Perez-Pariente, Joaquin, et al. "Organising disordered matter: strategies for ordering the network of mesoporous materials." (Comptes Rendus-Chimie) Mar. 1, 2005, pp. 569-578, vol. 8, No. 3-4.
Zheng, Junlin et al. "Hydrothermally stable MCM-41 analogue with extensive embedded voids." (Catalysis Today), Sep. 1, 2004, pp. 529-534, vol. 93-95.
Liu, Yu et al. "Steam-Stable MSU-S Aluminosilicate Mesostructures Assembled from Zeolite ZSM-5 and Zeolite Beta Seeds." (Agewandte Chemie International Edition), 2001, pp. 1255-1258, vol. 40, No. 7.

* cited by examiner

*Primary Examiner* — In Suk Bullock
*Assistant Examiner* — Bradley Etherton
(74) *Attorney, Agent, or Firm* — Millen, White, Zelano & Branigan, P.C.

(57) ABSTRACT

A process for oligomerization of an olefinic feedstock that contains olefinic hydrocarbon molecules that have 2 to 10 carbon atoms per molecule is described, whereby said process comprises bringing said feedstock into contact with a catalyst that comprises at least one amorphous material with hierarchized and organized porosity and consists of at least two elementary spherical particles, each of said particles comprising a mesostructured silicon-oxide-based matrix that has a mesopore diameter of between 1.5 and 30 nm and that exhibits amorphous and microporous walls with a thickness of between 1 and 50 nm, whereby said elementary spherical particles have a maximum diameter of 200 microns.

15 Claims, No Drawings

PROCESS FOR OLIGOMERIZATION OF LIGHT OLEFINS USING A CATALYST BASED ON AN AMORPHOUS MATERIAL WITH HIERARCHIZED AND ORGANIZED POROSITY

TECHNICAL FIELD

This invention relates to any process for oligomerization of olefins that makes possible the production of fuel, for example the production of gasoline and/or kerosene, starting from light olefinic feedstocks that contain between 2 and 10 carbon atoms per molecule using an oligomerization catalyst that comprises at least one amorphous metallosilicate material that has a hierarchized and organized porosity in the fields of microporosity and mesoporosity.

PRIOR ART

In the quest for new aluminosilicate materials, the so-called "mesostructured" materials, discovered at the beginning of the 1990s, represent a seductive alternative (G. J. of A. A. Soler-Illia, C. Sanchez, B. Lebeau, J. Patarin, Chem. Rev., 2002, 102, 4093). Actually, owing to so-called "soft chemistry" synthesis methods, amorphous mesoporous materials whose size and morphology of the pores are monitored have been obtained. These mesostructured materials are thus generated at low temperature by the coexistence in aqueous solution or in polar solvents of inorganic precursors with structuring agents, generally molecular or supramolecular, ionic or neutral surfactants. The monitoring of the electrostatic interactions or hydrogen bonds between the inorganic precursors and the structuring agent jointly linked to hydrolysis/condensation reactions of the inorganic precursor leads to a cooperative assembly of organic and inorganic phases that generate micellar aggregates of surfactants of uniform size that is monitored within an inorganic matrix. This cooperative self-assembly phenomenon, governed by, i.a., the concentration of structuring agent, can be induced by gradual evaporation of a solution of reagents whose structuring agent concentration is less than the critical micellar concentration, which can lead to, for example, the formation of a mesostructured powder after atomization of the solution (aerosol technique). The release of the porosity is then obtained by elimination of the surfactant, the latter being carried out conventionally by processes for chemical extraction or by heat treatment. Based on the nature of inorganic precursors and the structuring agent that is employed as well as the operating conditions that are imposed, several families of mesostructured materials have been developed. For example, the M41S family—initially developed by Mobil (J. S. Beck, J. C. Vartuli, W. J. Roth, M. E. Leonowicz, C. T. Kresge, K. D. Schmitt, C. T.-W. Chu, D. H. Olson, E. W. Sheppard, S. B. McCullen, 3. B. Higgins, J. L. Schlenker, J. Am. Chem. Soc., 1992, 114, 27, 10834), consisting of mesoporous materials obtained via the use of ionic surfactants such as quaternary ammonium salts, having a generally hexagonal, cubic or lamellar structure, pores with a uniform size encompassed in a range of 1.5 to 10 nm and amorphous walls with a thickness on the order of 1 to 2 nm—has been extensively studied. Likewise, the use of block-copolymer-type amphiphilic macromolecular structuring agents has led to the development of the family of materials referred to as SBA, whereby these solids are characterized by a generally hexagonal, cubic or lamellar structure, pores with a uniform size encompassed in a range of 4 to 50 nm, and amorphous walls with a thickness encompassed in a range of 3 to 7 nm.

It has been shown, however, that although exhibiting particularly advantageous textural and structural properties (in particular for the treatment of heavy feedstocks), the mesostructured aluminosilicate materials that are thus obtained developed a catalytic activity that was similar in all respects to that of their homologues with non-organized porosity (D. Zaho, J. Feng, Q. Huo, N. Melosh, G. H. Fredrickson, B. F. Chmelke, G. D. Stucky, Science, 1998, 279, 548; Y.-H. Yue, A. Gédéon, J.-L. Bonardet, J. B. d'Espinose, N. Melosh, J. Fraissard, Stud. Surf. Sci. Catal., 2000, 129, 209). Numerous works have therefore been undertaken for the purpose of developing materials that have a microporosity that is zeolitic in nature and a mesostructured porosity so as to benefit simultaneously from catalytic properties that are specific to zeolites and catalytic properties and primarily textural properties of the organized mesoporous phase.

A large number of synthesis techniques that make it possible to generate materials that have this bi-porosity have thus been listed in the literature (U.S. Pat. No. 6,669,924; Z. Zhang, Y. Han, F. Xiao, S. Qiu, L. Zhu, R. Wang, Y. Yu, Z. Zhang, B. Zou, Y. Wang, H. Sun, D. Zhao, Y. Wei, J. Am. Chem. Soc., 2001, 123, 5014; A. Karlsson, M. Stöcker, R. Schmidt, Micropor. Mesopor. Mater., 1999, 27, 181; P. Prokesova, S. Mintova, J. Cejka, T. Bein, Micropor. Mesopor. Mater., 2003, 64, 165; D. T. On, S. Kaliaguine, Angew. Chem. Int. Ed., 2002, 41, 1036). From an experimental standpoint, unlike the previously cited "aerosol" technique, the thus defined aluminosilicate materials with hierarchized porosity are not obtained by a gradual concentration of the inorganic precursors and the structuring agent(s) within the solution where they are present but are conventionally obtained by direct precipitation within an aqueous solution or in polar solvents by varying the value of the critical micellar concentration of the structuring agent. In addition, the synthesis of these materials that are obtained by precipitation requires a curing stage in an autoclave as well as a stage for filtration of the generated suspension. The elementary particles that are usually obtained do not have a uniform shape and are generally characterized by a size that generally varies between 200 and 500 nm and sometimes more.

The processes for oligomerization of the light olefins intended for the production of olefins of higher molecular weight are used extensively in the field of refining and petrochemistry for the purpose of upgrading the light olefins in terms of bases for gasoline-, kerosene- or gas-oil-type fuels, or else in terms of solvent. These oligomerization reactions are conducted in the presence of a catalyst, most often a solid catalyst. The olefins are combined into dimers, trimers, tetramers, etc., the degree of polymerization of the olefins depending on the type of catalyst that is used and the operating conditions of temperature and pressure that are imposed. The advantage of the oligomerization process, relative to other processes in the field of refining and petrochemistry leading to the same product range and well known to one skilled in the art, resides in the fact that the thus obtained compounds are free of sulfur and contain very few aromatic compounds. The solid oligomerization catalysts that are often cited in literature are acidic catalysts whose major examples in the field of oligomerization of light olefins are the "solid substrate-impregnated phosphoric acid" catalysts (for example, U.S. Pat. No. 2,913,506 and U.S. Pat. No. 3,661, 801), the silica-aluminas (for example, the U.S. Pat. No. 4,197,185, U.S. Pat. No. 4,544,791, and EP 0,463,673), the zeolites (for example, the U.S. Pat. No. 4,642,404 and U.S. Pat. No. 5,284,989), and, to a lesser extent, the heteropolyanions (for example, the patent IN 170,903).

The catalysts of the type "phosphoric acid impregnated on a solid substrate" (SPA) have a good oligomerization activity as well as a high yield of products that can be upgraded in the gasoline fraction. These catalysts are difficult to manipulate, however, in particular at the time of unloading, because of their tendency to cake in the presence of olefins. The catalysts of the type "phosphoric acid impregnated on a solid substrate" degrade during the reaction and cannot be regenerated.

The zeolites are acid materials, active for the oligomerization reaction of light olefins because of the nature of the engaged sites. These catalysts are therefore used for such applications. An appropriate selection of the zeolitic catalyst makes it possible, via suitable geometric selectivity, to increase the production of slightly branched oligomers while still limiting the diffusional limitations within the microporous network. A careful selection of the nature of the zeolite as an oligomerization catalyst therefore makes it possible to modulate the selectivity of the reaction and can therefore lead to oligomers that have a level of branching that is lower than that of oligomers obtained from reactions that are catalyzed by catalysts that do not impose any selectivity of form. This gain in selectivity is favorable in a context of production of good-quality gas oils, i.e., a high octane number, but it is not very favorable, for example, in the production of gasoline that has a good octane number.

The generic term silica-alumina covers a wide range of amorphous aluminosilicate catalysts that have textural and physicochemical properties that are suited to the oligomerization reaction. The properties of texture and acidity of the material, dictated by the method of preparation of the catalyst and well known to one skilled in the art, condition the activity and the selectivity of the catalyst. It is known, however, that the catalysts that are based on amorphous silica-alumina and that have a large pore volume impose fewer geometric constraints than their zeolitic homologues and are therefore advantageous candidates for the production of gasoline and/or kerosene through the reaction of oligomerization of light olefins. For example, the catalysts that are claimed by the patent EP 0,463,673 for the oligomerization of propylene into products that can be upgraded in the gasoline and/or kerosene pool are amorphous silica-aluminas that are characterized by large specific surface areas, between 500 and 1,000 m²/g, a total pore volume of between 0.3 and 0.6 ml/g, a mean pore diameter that is at most equal to approximately 1 nm, and no pore that has a diameter of greater than 3 nm.

The heteropolyanion-type catalysts are used for the oligomerization reaction of light olefins. These catalysts are not thermally stable and therefore lead to weak conversions and oligomers with a limited degree of polymerization due to the restricted working temperature.

SUMMARY

This invention has as its object a process for oligomerization of an olefinic feedstock that contains olefinic hydrocarbon molecules that have 2 to 10 carbon atoms per molecule, whereby said process comprises bringing said feedstock into contact with a catalyst that comprises at least one amorphous material with hierarchized and organized porosity and consists of at least two elementary spherical particles, each of said particles comprising a mesostructured silicon-oxide-based matrix that has a mesopore diameter of between 1.5 and 30 nm and that has amorphous and microporous walls with a thickness of between 1 and 50 nm, whereby said elementary spherical particles have a maximum diameter of 200 microns. The amorphous walls of said silicon-oxide-based matrix consist entirely of protozeolitic entities at the origin of the microporosity. The latter are radicals that are prepared from reagents that are used for the synthesis of zeolites or related solids, the preparation of said radicals not having been conducted up to the stage of the formation of crystallized zeolites or related crystallized solids. Thus, the formulations that lead to any zeolite or related solid developing acidity properties can be used. Said silicon-oxide-based matrix also comprises at least one element X, whereby the chemical nature of X is based on the composition of said formulations that are employed and can be, in a non-exhaustive way, one of the following elements: aluminum, iron, germanium, boron and titanium. Advantageously, X is the element aluminum.

ADVANTAGE

It has been discovered, surprisingly enough, that a catalyst that comprises at least one amorphous metallosilicate material with hierarchized and organized porosity leads to improved catalytic performances in terms of conversion and yields when it is implemented in a process for oligomerization of an olefinic feedstock that contains olefinic molecules that have 2 to 10 carbon atoms per molecule, whereby said process makes possible the production of fuel, for example the production of gasoline and/or kerosene.

The amorphous material with hierarchized and organized porosity that is present in the catalyst that is used in the oligomerization process according to the invention and that is formed by a mesostructured inorganic matrix, based on silicon oxide, with amorphous and microporous walls, simultaneously exhibits structural and textural properties that are suitable for microporous and mesostructured materials. Said silicon-oxide-based material exhibits acido-basicity properties that are superior to the acido-basicity properties that are exhibited by the prior amorphous aluminosilicate materials, lacking in precursors of protozeolitic entities, and prepared according to the synthesis protocols that are well known to one skilled in the art using inorganic precursors of silica and alumina.

The catalyst that is used in the oligomerization process according to the invention exhibits particular physico-chemical properties coupled to suitable textural properties that explain the high catalytic performance levels of said catalyst for the implementation of the oligomerization reaction of olefins that have 2 to 10 carbon atoms per molecule. In particular, said catalyst that is used in the oligomerization process according to the invention is very active: the conversion of the olefinic feedstock that contains hydrocarbon molecules that have 2 to 10 carbon atoms per molecule, and preferably 2 to 8 carbon atoms per molecule, is high, which is advantageous for preventing the presence of a recycling loop in the installation of the unit implementing the oligomerization reaction. In addition, by using a catalyst that is as active as the catalyst that comprises said amorphous material with hierarchized and organized porosity, it is easier to work under milder operating conditions, in particular of temperature, than when a prior amorphous catalyst based on silica-alumina and lacking protozeolitic entities is used. The final yield of oligomerates that can be incorporated in the gasoline and/or kerosene fraction is also significantly improved.

Furthermore, the presence within the same spherical particle with a micrometric, and even nanometric, size of mesopores organized in a microporous and amorphous inorganic matrix leads to a preferred access of the reagents and products of the reaction at microporous sites during the use of the material as a primary element of the catalyst in the processes for oligomerization of olefinic feedstocks that contain hydrocarbon molecules that have 2 to 10 carbon atoms per molecule, and in a preferred manner that contain 2 to 8 carbon atoms per molecule. The improvement of the intraparticulate diffusion of the reagents and products within the amorphous material with organized and hierarchized porosity that is present in the catalyst that is used in the oligomerization process of the invention contributes to the improvement of the conversion of olefins into fuel and therefore to the increase in the yield of oligomerates. In addition, the presence of organized mesopores in a microporous and amorphous inorganic matrix makes it possible to conduct the oligomerization reaction in the absence of geometric constraints linked to the structure and therefore to promote the production of gasoline and/or kerosene during this reaction. In addition, the material that is present in the catalyst that is used in the oligomerization process of the invention consists of spherical elementary particles, whereby the diameter of these particles is at most equal to 200 µm, preferably less than 100 µm, advantageously varying from 50 nm to 20 µm, very advantageously from 50 nm to 10 µm, and in an even more advantageous manner from 50 nm to 3 µm. The limited size of these particles as well as their homogenous spherical shape make it possible to have a better diffusion of the reagents and products of the reaction during the use of the material as the primary element of the catalyst that is used in the process for oligomerization of olefinic feedstocks that contain hydrocarbon molecules that have 2 to 10 carbon atoms per molecule, and in a preferred manner that contain 2 to 8 carbon atoms per molecule comparatively to catalysts that are known in the prior art. The improvement of the interparticulate diffusion of the reagents and products within the material that is present in the catalyst that is used in the oligomerization process according to the invention contributes to the improvement of the catalytic performance levels of said catalyst.

Techniques of Characterization

The amorphous material with hierarchized porosity in the fields of microporosity and mesoporosity and organized within the field of mesoporosity that is present in the catalyst that is used in the oligomerization process according to the invention is characterized by several analytical techniques and in particular by low-angle x-ray diffraction (low-angle XRD), by nitrogen volumetric analysis (BET), by Transmission Electron Microscopy (TEM), by Scanning Electron Microscopy (SEM), and by X fluorescence (XE).

The nitrogen volumetric analysis that corresponds to the physical adsorption of nitrogen molecules in the porosity of the material via a gradual increase, of pressure at constant temperature provides information on the particular textural characteristics (mesopore diameter, type of porosity, specific surface area) of the amorphous material that is present in the catalyst that is used in the oligomerization process according to the invention. In particular, it makes it possible to access the total value of the micropore and mesopore volumes of the amorphous material that is present in the catalyst according to the invention. The form of the nitrogen adsorption isotherm and the hysteresis loop can provide information on the presence of the microporosity that is linked to the protozeolitic entities that constitute the amorphous walls of the matrix of each of the spherical particles of the amorphous material that is present in the catalyst that is used in the oligomerization process according to the invention and on the nature of the mesoporosity. In the disclosure that follows, the diameter of the mesopores $\phi$ of the amorphous material that is present in the catalyst that is used in the oligomerization process according to the invention corresponds to the mean diameter in the desorption of nitrogen that is defined as being a diameter such that all of the pores that are smaller than this diameter constitute 50% of the pore volume (Vp) that is measured on the desorption branch of the nitrogen isotherm. The quantitative analysis of the microporosity of the amorphous material that is present in the catalyst according to the invention is performed starting from the "t" method (Lippens-De Boer method, 1965) or "$\alpha_s$" method (method proposed by Sing), which correspond to initial adsorption isotherm transforms as described in the work "*Adsorption by Powders and Porous Solids. Principles, Methodology and Applications*," written by F. Rouquerol, J. Rouquerol, and K. Sing, Academic Press, 1999. These methods make it possible to access in particular the value of the micropore volume that is characteristic of the microporosity of the amorphous material that is present in the catalyst that is used in the oligomerization process according to the invention as well as the specific surface area of the sample. The reference solid that is used is a LiChrospher Si-1000 silica (M. Jaroniec, M. Kruck, J. P. Olivier, *Langmuir*, 1999, 15, 5410). Relative to the mesostructured matrix of the amorphous material that is present in the catalyst that is used in the oligomerization process according to the invention, the difference between the value of the diameter of the mesopores $\phi$ and the correlation distance between mesopores d defined by low-angle XRD as described below makes it possible to access the value e where e=d−$\phi$ and is characteristic of the thickness of the amorphous walls of the mesostructured matrix of the amorphous material that is present in the catalyst that is used in the oligomerization process according to the invention. Likewise, the curve $V_{ads}$ (ml/g)=f($\alpha_s$) that is obtained via the method $\alpha_s$ cited above is characteristic of the presence of microporosity within the amorphous material that is present in the oligomerization catalyst and leads to a value of the micropore volume that is encompassed in a range of 0.01 to 0.4 ml/g. The determination of the total micropore and mesopore volume and of the micropore volume as described above leads to a value of the mesopore volume of the amorphous material that is present in the catalyst that is used in the oligomerization process according to the invention in a range of 0.01 to 1 ml/g.

The technique of low-angle x-ray diffraction (values of the angle 2θ of between 0.5 and 3°) makes it possible to characterize the periodicity on the nanometric scale that is generated by the organized mesoporosity of the amorphous material that is present in the catalyst that is used in the oligomerization process according to the invention. In the following disclosure, the x-ray analysis is done on powder with a diffractometer that operates by reflection and that is equipped with a rear monochromator by using the radiation of copper (wavelength of 1.5406 Å). The peaks that are usually observed on the diffractograms that correspond to a given value of the angle 2θ are associated with inter-reticular distances $d_{(hkl)}$ that are characteristic of the structural symmetry of the material, ((hkl) being the Miller indices of the reciprocal network) by Bragg's equation: $2d_{(hkl)}*\sin(\theta)=\eta*\lambda$. This indexing then makes it possible to determine the mesh parameters (abc) of the direct network, the value of these parameters being based on the hexagonal, cubic or vermicular structure that is obtained and that is characteristic of the periodic organization of the mesopores of the amorphous material that is present in the catalyst that is used in the oligomerization process according to the invention.

The analysis by Transmission Electron Microscopy (TEM) is a technique that is also extensively used for characterizing the mesostructuring of the amorphous material that is present in the catalyst that is used in the oligomerization process according to the invention. The TEM allows the formation of an image of the solid that is under study, whereby the observed contrasts are characteristic of the structural organization, the texture, and the morphology of the observed particles, and the resolution of the technique reaches at most 0.2 nm. The analysis of the image also makes it possible to access the parameters d and ϕ that are characteristic of the amorphous material that is present in the oligomerization catalyst defined above.

The composition of the amorphous material that is present in the catalyst and that is used in the oligomerization process according to the invention can be determined by X fluorescence (XF).

The material that is present in the catalyst that is used in the oligomerization process according to the invention and the catalyst that is used in the oligomerization process according to the invention have been analyzed by NMR MAS of the $^{27}$Al solid on a Brüker company spectrometer such as the MSL 400, with a 4 mm probe. The speed of rotation of the samples is on the order of 11 kHz. Potentially, the NMR of the aluminum makes it possible to distinguish three types of aluminum of which the chemical displacements are presented below:

Between 100 and 40 ppm, tetracoordinated-type aluminum atoms, referred to as $Al_{IV}$, Between 40 and 20 ppm, pentacoordinated-type aluminum atoms, referred to as $Al_V$, Between 20 and −100 ppm, hexacoordinated-type aluminum atoms, referred to as $Al_{VI}$.

The aluminum atom is a quadripolar core. Under certain analytical conditions (low radiofrequency field: 30 kHz, low impulse angle: π/2 and water-saturated sample), the NMR technique of magic angle spinning (MAS) is a quantitative technique. The decomposition of the NMR MAS spectra makes it possible to access the quantity of different radicals directly. The spectrum is locked in chemical displacement relative to a 1 M aluminum nitrate solution. The aluminum signal is at 0 ppm.

DESCRIPTION OF THE INVENTION

This invention has as its object a process for oligomerization of an olefinic feedstock that contains olefinic hydrocarbon molecules that have 2 to 10 carbon atoms per molecule, whereby said process comprises bringing said feedstock into contact with a catalyst that comprises at least one amorphous material with hierarchized and organized porosity and that consists of at least two elementary spherical particles, each of said particles comprising a mesostructured silicon-oxide-based matrix, having a mesopore diameter of between 1.5 and 30 nm and exhibiting amorphous and macroporous walls with a thickness of between 1 and 50 nm, whereby said elementary spherical particles have a maximum diameter of 200 microns.

The material that is present in the catalyst that is used in the oligomerization process according to the invention is a material with hierarchized porosity in the fields of microporosity and mesoporosity and organized porosity in the field of mesoporosity. Within the meaning of this invention, material with hierarchized and organized porosity is defined as a material that exhibits a double porosity on the scale of each of said spherical particles: a mesoporosity, i.e., the presence of pores organized on the mesoporous scale that have a uniform diameter of between 1.5 and 30 nm, preferably between 4 and 30 nm, and in a very preferred manner between 5 and 20 nm, distributed homogeneously and uniformly in each of said particles (mesostructuring), and a microporosity that is induced by the amorphous walls, whereby the characteristics of this microporosity are based on protozeolitic entities that constitute amorphous walls of the matrix of each of the spherical particles of the material with hierarchized and organized porosity that is present in the catalyst that is used for the implementation of the oligomerization process according to the invention. The microporosity is characterized by the presence of micropores, within said amorphous walls, having a diameter that is less than 1.5 nm. The material that is present in the catalyst that is used for the implementation of the oligomerization process according to the invention also exhibits an interparticulate and intraparticulate textural macroporosity. It should be noted that a porosity that is microporous in nature can also result from the interleaving of the surfactant, used during the preparation of the material with hierarchized and organized porosity that is present in the catalyst that is used for the implementation of the oligomerization process according to the invention, with the inorganic wall at the level of the organic-inorganic interface that is developed during the mesostructuring of the inorganic component of said material with hierarchized and organized porosity that is present in the catalyst that is used for the implementation of the oligomerization process according to the invention. Advantageously, none of the spherical particles that constitute the material that is present in the catalyst that is used for the implementation of the oligomerization process according to the invention has macropores.

According to the invention, the silicon-oxide-based matrix that forms each of the spherical particles of the material with hierarchized and organized porosity that is present in the catalyst that is used for the implementation of the oligomerization process according to the invention exhibits amorphous walls that consist entirely of protozeolitic entities, which are at the origin of the microporosity that is present within each of the spherical particles of said material that is present in said catalyst that is used for the implementation of the oligomerization process according to the invention. The protozeolitic entities are radicals that are prepared from reagents that are used for the synthesis of zeolites or related solids, whereby the preparation of said radicals has not been conducted up to the stage of the formation of crystallized zeolites or related crystallized solids. The result is that said small protozeolitic entities are not detected when they are characterized by large-angle x-ray diffraction. More specifically and according to the invention, the protozeolitic entities that constitute integrally and homogeneously the amorphous microporous walls of the matrix of each of the spherical particles of the material that is present in the catalyst that is used for the implementation of the oligomerization process according to the invention are radicals that result from bringing at least one structuring agent, at least one silicic precursor and at least one precursor of at least one element X that is selected from among aluminum, iron, germanium, titanium and boron, preferably an aluminum precursor, under variable conditions of time and temperature making it possible to end in a clear solution, into the presence of said radicals that can be used to initiate the synthesis of any zeolite or related solid that develops acidity properties and in particular but in a non-restrictive way any zeolite or related solid listed in "Atlas of Zeolite Framework Types," 6$^{th}$ Edition, 2007, Ch. Baerlocher, L. B. McCusker & D. H. Olson, Amsterdam: Elsevier.

According to the invention, the silicon-oxide-based matrix that forms each of the elementary spherical particles of said material that is present in said catalyst used for the implementation of the oligomerization process according to the invention comprises at least one element X that is selected from among aluminum, iron, germanium, titanium and boron, preferably aluminum. Thus, the protozeolitic entities that integrally constitute the amorphous and microporous walls of the matrix of each of the spherical particles of the material that is present in said catalyst and at the origin of the microporosity of said material are advantageously radicals for initiating at least one zeolite that contains silicon and at least one element X that is selected from among aluminum, iron, germanium, titanium and boron, preferably aluminum. When X is aluminum, the matrix of the material that is present in the catalyst that is used for the implementation of the oligomerization process according to the invention is an amorphous aluminosilicate, precursor of a crystallized aluminosilicate material. This amorphous aluminosilicate exhibits an Si/Al molar ratio that is equal to that of the solution of the silicic and aluminum precursors leading to the formation of protozeolitic entities that integrally constitute the amorphous and microporous walls of the matrix.

Zeolites or related solids that are well known to one skilled in the art are defined as all of the crystallized microporous oxide solids whose atomic elements that constitute the inorganic framework exhibit a coordination number IV. By definition, the designation "zeolite" is attributed to said silicic or metallosilicic microporous oxide solids, in particular aluminosilicic solids. Likewise, the designation "related solid" relates to all of the crystallized microporous oxide solids whose constituent atomic elements of the inorganic framework exhibit a coordination number IV, whereby said uniquely silicic or metallosilicic, preferably aluminosilicic, microporous oxide solids are excluded. Any zeolite or related solid that exhibits at least one trivalent atomic element at the origin of the presence of a negative charge of said framework and that can be compensated by a positive charge of a protonic nature can develop acidity properties. In particular, the metallosillicate-type zeolites, preferably aluminosilicate-type zeolites, and the related silicoaluminophosphate-type solids develop such properties.

The protozeolitic entities that integrally constitute the amorphous walls of the matrix of each of the particles of the material that is present in the catalyst that is used for the implementation of the oligomerization process according to the invention and at the origin of the microporosity of said material are preferably radicals for initiating at least one zeolite that is selected from among the metallosilicates ZSM-5, ZSM-11, ITQ-13, MCM-22, SSZ-44, SSZ-35, ZSM-22, ZSM-23, ZBM-30, ZSM-35, ZSM-48, ZSM-57, EU-1, EU-2, EU-11, beta, zeolite A, Y, USY, VUSY, SDUSY, mordenite, NU-87, NU-88, NU-86, NU-85, IM-5, IM-12, IZM-2 and ferrierite and/or radicals for initiating at least one related solid that is selected from among the silicoaluminophosphates SAPO-11 and SAPO-34. Said protozeolitic entities integrally constituting the amorphous and microporous walls of the matrix of each of the particles of said material that is present in the catalyst that is used for the implementation of the oligomerization process according to the invention are radicals for initiating at least one zeolite that is selected from among the metallosilicates of the structural type MEL, MFI, ITH, BEA, NES, EUO, ERI, FER, CHA, MFS, MWW, MTT, TON, SFF, STF and MOR, and in a very preferred manner selected from among the zeolites of the structural type TON, MTT, BEA, MFS, MFI, MOR and FER. Among the MEL-structural-type zeolites, the ZSM-11 zeolite is preferred. Among the MFI-structural-type zeolites, the ZSM-5 zeolite is preferred. Among the ITH-structural-type zeolites, the ITQ-13 zeolite is preferred (U.S. Pat. No. 6,471,941). Among the NES-structural-type zeolites, the NU-87 zeolite is preferred. Among the EUO-structural-type zeolites, the EU-1 zeolite is preferred. Among the ERI-structural-type zeolites, the erionite zeolite is preferred. Among the FER-structural-type zeolites, the ferrierite and ZSM-35 zeolites are preferred. Among the CHA-structural-type zeolites, the chabazite zeolite as well as the SAPO-34 siliocoaluminophosphate are preferred. Among the MFS-structural-type zeolites, the ZSM-57 zeolite is preferred. Among the MWW-structural-type zeolites, the MCM-22 zeolite is preferred. Among the MTT-structural-type zeolites, the ZSM-23 zeolite is preferred. Among the TON-structural-type zeolites, the ZSM-22 zeolite is preferred. Among the MOR-structural-type zeolites, the mordenite zeolite is preferred. These zeolites and their methods of preparation are well known to one skilled in the art.

The silicon-oxide-based matrix, encompassed in each of the spherical particles constituting said material that is present in said catalyst that is used for the implementation of the oligomerization process according to the invention, is mesostructured: it exhibits mesopores that have a uniform diameter of between 1.5 and 30 nm, preferably between 4 and 30 nm, and in a very preferred manner between 5 and 20 nm, distributed homogeneously and uniformly in each of the spherical particles. The material that is located between the mesopores of each of said spherical particles is microporous and integrally amorphous and forms walls, or panels, whose thickness is between 1 and 50 nm, preferably between 2.5 and 30 nm, and in a very preferred manner between 4 and 30 nm. The thickness of the walls corresponds to the distance that separates a first mesopore from a second mesopore, whereby the second mesopore is the pore that is the closest to said first mesopore. The organization of the mesoporosity that is described above leads to a structuring of the silicon-oxide-based matrix, which can be hexagonal, vermicular, or cubic, and preferably vermicular. The small-angle XRD analysis makes it possible to calculate the distance d for correlation between the organized mesopores of said material: the distance d for correlation between the organized mesopores of said material is between 6 and 50 nm, preferably between 8 and 30 nm, and in a very preferred manner between 9 and 25 nm.

The NMR MAS analysis of the solid of $^{27}$Al, in the case where the element X is aluminum, leads to obtaining NMR$^{27}$Al spectra of the material that is present in the oligomerization catalyst and the oligomerization catalyst that is characterized by the presence of 2 or 3 peaks respectively combined with the presence of aluminum atoms at coordination numbers IV and VI or in the presence of aluminum atoms at coordination numbers IV, V and VI. The chemical displacements of said atoms at the thus observed coordination numbers IV, V and VI are respectively on the order of 50, 30 and 0 ppm. The quantitative determination of the different aluminum atoms indicates that the aluminum radicals at coordination number V and/or VI represent at least 10 mol %, preferably at least 15 mol %, and even more preferably at least 20 mol % of all of the aluminum radicals.

Furthermore, the material that is present in the oligomerization catalyst and the oligomerization catalyst do not lead to any signal when they are analyzed by FTIR (Fourier Transform Infrared). In particular, they do not exhibit the visible band by FTIR analysis at 550-600 cm$^{-1}$ that is characteristic of the pentasil radicals of MR-type zeolitic entities.

According to the invention, said elementary spherical particles that constitute the material with hierarchized and organized porosity that is present in the catalyst that is used for the implementation of the oligomerization process according to the invention have a maximum diameter that is equal to 200 microns, preferably less than 100 microns, advantageously between 50 nm and 20 µm, very advantageously between 50 nm and 10 µm, and in an even more advantageous manner between 50 nm and 3 µm. More specifically, they are present in the material that is present in the catalyst according to the invention in the form of aggregates.

The material with hierarchized and organized porosity that is present in the catalyst that is used for the implementation of the oligomerization process according to the invention and the catalyst that is used for the implementation of the oligomerization process according to the invention advantageously exhibit a specific surface area of between 100 and 1,100 m²/g and in a very advantageous manner of between 200 and 1,000 m²/g. Said material with hierarchized and organized porosity advantageously exhibits a mesopore volume that is measured by nitrogen volumetric analysis of between 0.01 and 1 ml/g, preferably between 0.01 and 0.8 ml/g, and a micropore volume that is measured by nitrogen volumetric analysis of between 0.01 and 0.4 ml/g.

The catalyst that is used for the implementation of the oligomerization process according to the invention advantageously exhibits a mean mesopore diameter of between 1.5 and 30 nm and in a very advantageous manner between 1.5 and 15 nm.

The catalyst that is used in the oligomerization process according to the invention advantageously comprises at least one binder that is selected from the group that is formed by alumina, silica, silica-alumina, clays, in particular natural clays such as kaolin or bentonite, magnesia, titanium oxide, boron oxide, zirconia, aluminum phosphates, titanium phosphates, zirconium phosphates, and carbon.

The catalyst that is used in the oligomerization process according to the invention advantageously comes in the form of cylindrical or multilobed extrudates such as bilobed, trilobed, or multilobed extrudates of straight or twisted shape or else in the form of crushed powders, tablets, rings, balls, and wheels. In a very preferred manner, the catalyst that is used in the oligomerization process according to the invention comes in the form of extrudates with a diameter of between 0.5 and 5 mm and more particularly between 0.7 and 2.5 mm. In a preferred manner, the cylindrical shape is used.

The catalyst that is used in the oligomerization process according to the invention also advantageously comprises at least one metal that is selected from among the metals of groups IA, IIA, IIB, VIIB and VIII. Among the metals of group IA, sodium is preferred. Among the metals of group IIA, magnesium, calcium, strontium, and barium are preferred. Among the metals of group IIB, zinc and cadmium are preferred. Among the metals VIIB, rhenium is preferred. Among the metals of group VIII, iron, cobalt, nickel, platinum, palladium, rhodium and ruthenium are preferred. The content by weight of metal(s) is advantageously between 0.01 and 10% by weight and very advantageously between 0.05 and 5% by weight relative to the weight of the amorphous material that is present in the catalyst that is used in the process according to the invention.

The material with hierarchized and organized porosity that comprises silicon and that is present in the catalyst that is used for the implementation of the process according to the invention is obtained according to a process for preparation that comprises: a) the preparation of a clear solution that contains the precursor elements of protozeolitic entities, namely at least one structuring agent, at least one silicic precursor, and at least one precursor of at least one element X that is selected from among aluminum, iron, germanium, titanium, and boron, preferably an aluminum precursor; b) the mixing in solution of at least one surfactant and at least said clear solution that is obtained according to a) such that the ratio of the volumes of inorganic and organic materials is between 0.26 and 4; c) the atomization by aerosol of said solution that is obtained in stage b) for leading to the formation of spherical droplets; d) the drying of said droplets; and e) the elimination of said structural agent and said surfactant for obtaining an amorphous material with hierarchized porosity in the range of microporosity and mesoporosity and organized within the range of mesoporosity. Below, this process is called "process for preparation of the material with hierarchized and organized porosity."

According to stage a) of the process for preparation of the material with hierarchized and organized porosity, the clear solution that contains the precursor elements of protozeolitic entities, namely at least one structuring agent, at least one silicic precursor, and at least one precursor of at least one element X that is selected from among aluminum, iron, titanium, boron, and germanium, preferably an aluminum precursor, is implemented starting from operating protocols that are known to one skilled in the art.

The silicic precursor that is used for the implementation of stage a) of the process for preparation of the material with hierarchized and organized porosity is selected from among the silicon oxide precursors that are well known to one skilled in the art. In particular, a silicic precursor that is selected from among the silica precursors that are usually used in the synthesis of zeolites or related solids is advantageously used; for example, solid silica in powder form, silicic acid, colloidal silica, dissolved silica or tetraethoxysilane that is also called tetraethylorthosilicate (TEOS) is used. In a preferred manner, the silicic precursor is TEOS.

The precursor of the element X, used for the implementation of stage a) of the process for preparation of the material with hierarchized and organized porosity, can be any compound that comprises the element X and that can release this element in solution, in particular in aqueous solution or aquo-organic solution, in reactive form. In the case where X is aluminum, the aluminum precursor is advantageously an inorganic aluminum salt of formula $AlZ_3$, whereby Z is a halogen, a nitrate or a hydroxide. Preferably, Z is chlorine. The aluminum precursor can also be an aluminum sulfate of formula $Al_2(SO_4)_3$. The aluminum precursor can also be an organometallic precursor of formula $Al(OR)_3$, where R=ethyl, isopropyl, n-butyl, s-butyl ($Al(O^SC_4H_9)_3$) or t-butyl or a chelated precursor such as aluminum acetyl acetonate ($Al(C_5H_8O_2)_3$). Preferably, R is s-butyl. The aluminum precursor can also be sodium aluminate or ammonium aluminate or alumina itself in one of its crystalline phases that are known to one skilled in the art (alpha, delta, theta, gamma), preferably in hydrated form or that can be hydrated.

It is also possible to use mixtures of the precursors cited above. Some or all of the aluminum and silicic precursors can optionally be added in the form of a single compound that comprises both aluminum atoms and silicon atoms, for example an amorphous silica-alumina.

The structuring agent that is used for the implementation of stage a) of the process for preparation of the material with hierarchized and organized porosity can be ionic or neutral according to the nature of the zeolite or the related solid that would be obtained from said protozeolitic entities. It is common to use structuring agents of the following non-exhaustive list: nitrogen-containing organic cations such as tetrapropylammonium (TPA), elements of the family of alkalines (Cs, K, Na, etc.), crown ethers, diamines, as well as any other structuring agent that is well known to one skilled in the art for the synthesis of zeolite or a related solid.

The clear solution that contains precursor elements of protozeolitic entities is generally obtained according to stage a) of the process for preparation of the material with hierarchized and organized porosity by preparing a reaction mixture that contains at least one silicic precursor, at least one precursor of at least one element X that is selected from among aluminum, iron, boron, titanium and germanium, preferably an aluminum precursor, and at least one structuring agent. The reaction mixture is either aqueous or aquo-organic, for example a water-alcohol mixture. It is preferred to work in a basic reaction medium during the various stages of the process for preparation of the material with hierarchized and organized porosity so as to promote the development of the protozeolitic entities that constitute the amorphous and microporous walls of the matrix of each of the particles of the material that is present in the catalyst that is used for the implementation of the oligomerization process according to the invention. The basicity of the solution is advantageously ensured by the basicity of the structuring agent that is employed or else by basification of the reaction mixture by adding a basic compound, for example an alkaline metal hydroxide, preferably sodium hydroxide. The reaction mixture can be put under hydrothermal conditions under an autogenous pressure, optionally by adding a gas, for example nitrogen, at a temperature of between ambient temperature and 200° C., preferably between ambient temperature and 170° C., and in an even more preferred manner at a temperature that does not exceed 120° C. until the formation of a clear solution that contains the precursor elements of the protozeolitic entities constituting the amorphous and microporous walls of the matrix of each of the spherical particles of the material that is present in the catalyst according to the invention is achieved. According to a preferred operating mode, the reaction mixture that contains at least one structuring agent, at least one silicic precursor, and at least one aluminum is cured at ambient temperature so as to obtain a clear solution that contains the precursor elements of protozeolitic entities that can generate the formation of crystallized zeolitic entities or crystallized related solids.

According to stage a) of the process for preparation of the material with hierarchized and organized porosity, the precursor elements of the protozeolitic entities that are present in the clear solution are synthesized according to operating protocols that are known by one skilled in the art. In particular, for a material according to the invention whose matrix of each spherical particle consists of beta protozeolitic entities, a clear solution that contains precursor elements of beta protozeolitic entities is implemented from the operating protocol described by P. Prokesova, S. Mintova, J. Cejka, T. Bein et coll., *Micropor. Mesopor. Mater.*, 2003, 64, 165. For a material according to the invention whose matrix of each spherical particle consists of FAU-type protozeolitic entities, a clear solution that contains precursor elements of FAU-type protozeolitic entities is implemented from operating protocols that are described by Y. Liu, W. Z. Zhang, T. J. Pinnavaia et coll., *J. Am. Chem. Soc.,* 2000, 122, 8791 and K. R. Kloetstra, H. W. Zandbergen, J. C. Jansen, H. van Bekkum, *Microporous Mater.,* 1996, 6, 287. For a material according to the invention whose matrix of each spherical particle consists of ZSM-5 protozeolitic entities, a clear solution that contains the precursor elements of ZSM-5 protozeolitic entities is produced from the operating protocol that is described by A. E. Persson, B. J. Schoeman, J. Sterte, J.-E. Otterstedt, *Zeolites,* 1995, 15, 611.

According to stage b) of the process for preparation of the material with hierarchized and organized porosity, the surfactant that is used is an ionic or non-ionic surfactant or a mixture of the two; preferably the surfactant that is used is a non-ionic surfactant. Preferably, the ionic surfactant is selected from among the anionic surfactants such as the sulfates, such as, for example, sodium dodecyl sulfate (SDS). Preferably, the non-ionic surfactant can be any copolymer that has at least two parts with different polarities that impart to them properties of amphiphilic macromolecules. These copolymers can comprise at least one block that is part of the non-exhaustive list of the families of the following polymers: the fluorinated polymers ($-[CH_2-CH_2-CH_2-CH_2-O-CO-R1-$ with $R1=C_4F_9$, $C_8F_{17}$, etc.), the biological polymers such as the amino polyacids (polylysine, alginates, etc.), the dendrimers, and the polymers that consist of chains of poly(alkylene oxide). Any other copolymer that is amphiphilic in nature and that is known to one skilled in the art can be used if it makes it possible to obtain a stable solution in stage b) of the process for preparation of the material with hierarchized and organized porosity, such as poly(styrene-b-acrylamide) for example (S. Förster, M. Antionnetti, *Adv. Mater.,* 1998, 10, 195; S. Förster, T. Plantenberg, *Angew. Chem. Int. Ed,* 2002, 41, 688; H. Cölfen, *Macromol. Rapid Commun,* 2001, 22, 219). In a preferred manner, within the scope of this invention, a block copolymer that consists of poly(alkylene oxide) chains is used. Said block copolymer is preferably a block copolymer that has two, three or four blocks, each block consisting of a poly(alkylene oxide) chain. For a two-block copolymer, one of the blocks consists of a poly(alkylene oxide) chain that is hydrophilic in nature, and the other block consists of a poly(alkylene oxide) chain that is hydrophobic in nature. For a three-block copolymer, at least one of the blocks consists of a poly(alkylene oxide) chain that is hydrophilic in nature, while at least one of the other blocks consists of a poly(alkylene oxide) chain that is hydrophobic in nature. Preferably, in the case of a three-block copolymer, the poly(alkylene oxide) chains that are hydrophilic in nature are poly(ethylene oxide) chains that are denoted $(PEO)_x$, and $(PEO)_z$, and the poly(alkylene oxide) chains that are hydrophobic in nature are poly(propylene oxide) chains denoted $(PPO)_y$, poly(butylene oxide) chains, or mixed chains of which each chain is a mixture of several alkylene oxide monomers. In a very preferred manner, in the case of a three-block copolymer, the latter consist of two poly(ethylene oxide) chains and a polypropylene oxide) chain. More precisely, a compound of formula $(PEO)_x-(PPO)_y-(PEO)_z$, where x is between 5 and 300, and y is between 33 and 300, and z is between 5 and 300, is used. Preferably, the values of x and z are identical. Very advantageously, a compound in which x=20, y=70, and z=20 (P123) is used, and a compound in which x=106, y=70, and z=106 (F127) is used. The commercial non-ionic surfactants that are known under the name of Pluronic (BASF), Tetronic (BASF), Triton (Sigma), Tergitol (Union Carbide), and Brij (Aldrich) can be used as non-ionic surfactants in stage b) of the process for preparation of the material with hierarchized and organized porosity. For a four-block copolymer, two of the blocks consist of a poly(alkylene oxide) chain that is hydrophilic in nature, and the two other blocks consist of a poly(alkylene oxide) chain that is hydrophobic in nature.

The solution that is obtained at the end of stage b) of the process for preparation of the material with hierarchized and organized porosity, in which at least said surfactant and at least said clear solution that is obtained according to stage a) are mixed, can be acidic, neutral or basic. Preferably, said solution is basic and preferably exhibits a pH that is greater than 9, whereby this value of the pH is generally imposed by the pH of the clear solution that contains the precursor elements of protozeolitic entities obtained according to stage a) of the process for preparation of the material with hierarchized and organized porosity. The solution that is obtained at the end of stage b) can be aqueous or can be an organic water-solvent mixture, whereby the organic solvent is preferably a polar solvent, in particular an alcohol, preferably ethanol.

The quantity of organic compounds, i.e., of surfactant and of structuring agent, present in the mixture according to stage h) of the process for preparation of the material with hierarchized and organized porosity, is defined relative to the quantity of inorganic material that is present in said mixture following the addition of the clear solution that contains the precursor elements of protozeolitic entities obtained according to stage a) of the process for preparation of the material with hierarchized and organized porosity. The quantity of inorganic material corresponds to the quantity of material of the silicic precursor and to at least that of the precursor of the element X. The volumetric ratio $V_{inorganic}/V_{organic}$ in the mixture that is obtained after the implementation of stage b) is such that the binary organic-inorganic system that is formed during the atomization stage c) of the process for preparation of the material with hierarchized and organized porosity undergoes a process for mesostructuring by self-assembly of the surfactant together with the hydrolysis/condensation reactions of the various inorganic precursors. Said volumetric ratio $V_{inorganic}/V_{organic}$ is defined as follows: $V_{inorganic}/V_{organic}=(m_{inorg}*\rho_{org})/(m_{org}*\rho_{inorg})$, where $m_{inorg}$ is the final mass of the inorganic fraction in the form of condensed oxide(s) in the solid elementary particle obtained by atomization; $m_{org}$ is the total mass of the non-volatile organic fraction that is in the solid elementary particle that is obtained by atomization; $\rho_{org}$ and $\rho_{inorg}$ are the densities that are respectively associated with non-volatile organic and inorganic fractions. Within the scope of the invention, when the element X is aluminum and for a simplification of the calculations (approximations that are valid for a large majority of the non-volatile organic fractions and for an inorganic fraction of the "aluminosilicate network" type), it is considered that $\rho_{org}=1$, and $\rho_{inorg}=2$. Within the scope of the invention, $m_{inorg}$ generally corresponds to the mass of $SiO_2$ that is added to that of the mass of $AlO_2$, when X is aluminum, and $m_{org}$ corresponds to the mass of the structuring agent, for example TPAOH, added to the mass of the surfactant, for example, the surfactant F127. The polar solvent, preferably ethanol, as well as water and soda, are not taken into account in the calculation of said ratio $V_{inorganic}/V_{organic}$. The radicals that comprise an element X, advantageously the aluminum radicals, for the preparation of the material that is present in the catalyst according to the invention, after the implementation of said stage b), are not taken into account for the calculation of the volumetric ratio $V_{inorganic}/V_{organic}$ that is defined above. According to the invention, the quantity of organic material and the quantity of inorganic material in the mixture that is obtained after the implementation of stage b) is such that the ratio $V_{inorganic}/V_{organic}$ is encompassed in a range of 0.26 to 4, and preferably in a range of 0.30 to 2. According to stage b) of the process for preparation of the material with hierarchized and organized porosity, the initial concentration of surfactant, introduced into the mixture, defined by $c_o$, is such that $c_o$ is less than or equal to $c_{mc}$, with the parameter $c_{mc}$ representing the critical micellar concentration that is well known to one skilled in the art, i.e.; the boundary concentration beyond which the self-arrangement phenomenon of the molecules of the surfactant occurs in the solution that is obtained at the end of stage b). Before atomization, the concentration of surfactant molecules of the solution obtained at the end of stage b) of the process for preparation of the material with hierarchized and organized porosity therefore does not lead to the formation of particular micellar phases. In one preferred implementation of the process according to the invention, the concentration $c_o$ is less than the $c_{mc}$, the ratio $V_{inorganic}/V_{organic}$ is such that the composition of the binary system verifies the conditions of composition for which a mesostructuring mechanism is produced by cooperative self-assembly of the reagents ($V_{inorganic}/V_{organic}$ of between 0.26 and 4, preferably between 0.3 and 2), and said solution that is targeted in stage b) of the process for preparation of the material with hierarchized and organized porosity is a basic water-alcohol mixture.

The stage for atomization of the mixture according to stage c) of the process for preparation of the material with hierarchized and organized porosity produces spherical droplets. The size distribution of these droplets is log normal. The aerosol generator that is used here is a model 9306 A commercial device provided by TSI and having a 6-jet atomizer. The atomization of the solution is done in a chamber in which a carrier gas, a mixture of $O_2/N_2$ (dry air), is sent under a pressure P that is equal to 1.5 bar.

According to stage d) of the process for preparation of the material with hierarchized and organized porosity, the drying of said droplets is initiated. This drying is implemented by the transport of said droplets via the carrier gas, the $O_2/N_2$ mixture, in PVC pipes, which leads to the gradual evaporation of the solution, for example the basic aquo-organic solution obtained during stage b) of the process for preparation of the material with hierarchized and organized porosity, and thus to obtaining spherical elementary particles. This drying is completed by running said particles into a furnace whose temperature can be adjusted, the usual temperature range varying from 50 to 600° C. and preferably from 80 to 400° C., whereby the dwell time of these particles in the furnace is on the order of one second. The particles are then collected in a filter. A pump that is placed at the circuit's end helps channel the radicals into the experimental aerosol device. The drying of the droplets according to stage d) of the process for preparation of the material with hierarchized and organized porosity is advantageously followed by being run through the oven at a temperature of between 50 and 150° C.

In the particular case where the element X, used for the implementation of stage a) of the process for preparation of the material with hierarchized and organized porosity, is aluminum and where the sodium element is present in the clear solution that is obtained according to stage a) of the process for preparation of the material with hierarchized and organized porosity via the use of sodium hydroxide and/or a soda structuring agent that ensures the basicity of said clear solution, it is preferred to implement an additional stage of ion exchange that makes it possible to exchange the $Na^+$ cation by the $NH_4^+$ cation between the stages d) and e) of the process for preparation of the material with hierarchized and organized porosity. This exchange, which leads to the formation of $H^+$ protons after stage e) of the process for preparation of the material with hierarchized and organized porosity in the preferred case where the elimination of the structuring agent and of the surfactant is implemented by calcination in air, is implemented according to operating protocols that are well known to one skilled in the art. One of the usual methods consists in suspending the dried solid particles that are obtained from stage d) of the process for preparation of the material with hierarchized and organized porosity in an aqueous solution of ammonium nitrate. The mass is then brought to reflux for a period of 1 to 6 hours. The particles are then recovered by filtration (centrifuging at 9,000 rpm), washed, and then dried by running through the oven at a temperature of between 50 and 150° C. This ion exchange/washing/drying cycle can be conducted several times and preferably two other times. This exchange cycle can also be implemented after the stages d) and e) of the process for preparation of the material with hierarchized and organized porosity. Under these conditions, the stage e) is then reproduced after the last exchange cycle so as to generate the $H^+$ protons as explained above.

According to stage e) of the process for preparation of the material with hierarchized and organized porosity, the elimination of the structuring agent and the surfactant so as to obtain the material that is present in the catalyst and that is used in the oligomerization process according to the invention is advantageously implemented by chemical extraction processes or by heat treatment and preferably by calcination in air in a temperature range of 300 to 1,000° C. and more specifically in a range of 400 to 600° C. for a period of 1 to 24 hours and preferably for a period of 2 to 12 hours.

In the case where the solution targeted in stage b) of the process for preparation of the material with hierarchized and organized porosity is a water-organic solvent mixture, preferably basic, it is essential during stage b) of the process for preparation of the material with hierarchized and organized porosity that the concentration of surfactant at the origin of the mesostructuring of the matrix is less than the critical micellar concentration and that the ratio $V_{inorganic}/V_{organic}$ is encompassed in a range of 0.26 and 4, and preferably in a range of 0.30 to 2, such that the evaporation of said aquo-organic solution, preferably basic, during stage c) of the process for preparation of the material with hierarchized and organized porosity by the aerosol technique induces a phenomenon of micellization or self-assembly leading to the mesostructuring of the matrix of the material that is present in the catalyst according to the invention. When $c_o < c_{mc}$, the mesostructuring of the matrix of the material that is present in the catalyst that is used in the oligomerization process according to the invention follows a gradual concentration, within each droplet, of the precursor elements of protozeolitic entities of the clear solution that is obtained in stage a) of the process for preparation of the material with hierarchized and organized porosity and at least one surfactant that is introduced during stage h) of the process for preparation of the material with hierarchized and organized porosity, up to a surfactant concentration $c > c_{mc}$ that results from an evaporation of the preferably basic aquo-organic solution.

According to a first preferred embodiment of the process for preparation of the material with hierarchized and organized porosity, at least one precursor of at least one element X that is selected from among aluminum, iron, titanium, boron, and germanium, preferably an aluminum precursor, is introduced for the implementation of said stage b) of the process for preparation of the material with hierarchized and organized porosity. Thus, the mixing in solution of at least one surfactant and at least said clear solution that is obtained according to stage a) of said process is implemented in the presence of at least one precursor of said element X, advantageously an aluminum precursor that is selected in particular from among the aluminum precursors that are described above in this description, for the implementation of said stage a) of the process for preparation of the material with hierarchized and organized porosity.

According to a second preferred embodiment of the process for preparation of the material with hierarchized and organized porosity, at least one precursor of at least one element X that is selected from among aluminum, iron, titanium, boron, and germanium, preferably an aluminum precursor, is introduced during the implementation of said stage d) and/or said stage e) of the process for preparation of the material with hierarchized and organized porosity for the purpose of producing a surface modification of the material that is present in the catalyst that is used in the oligomerization process according to the invention. According to said second preferred embodiment of the process for preparation of the material with hierarchized and organized porosity, said precursor of at least said element X, preferably said aluminum precursor, is introduced during the implementation of said stage d) and/or said stage e) by any surface modification technique that is well known to one skilled in the art, such as the grafting of at least one precursor of at least one element X, dry impregnation of at least one precursor of at least one element X, and excess impregnation of at least one precursor of at least one element X. Said precursor of at least one element X that is selected from among aluminum, iron, boron, titanium and germanium, preferably an aluminum precursor, introduced during the implementation of said stage d) and/or said stage e) of the process for preparation of the material with hierarchized and organized porosity by a surface modification technique, is selected from among the aluminum precursors, described above in this description, for the implementation of said stage a) of the process for preparation of the material with hierarchized and organized porosity. According to said second preferred embodiment of the process for preparation of the material with hierarchized and organized porosity, stage b) of the process for preparation of the material with hierarchized and organized porosity is implemented in the presence or in the absence of at least one precursor of at least one element X, advantageously an aluminum precursor.

According to the process for preparation of the material with hierarchized and organized porosity, said first preferred embodiment of the process for preparation of the material with hierarchized and organized porosity and said second preferred embodiment of the process for preparation of the material with hierarchized and organized porosity are only optional variants of the process for preparation of the material with hierarchized and organized porosity. Also, when the mesostructured matrix of each of the spherical particles of the material that is present in the catalyst according to the invention comprises an element X, advantageously aluminum, said element X, advantageously aluminum, is introduced either during said stage a) of the process for preparation of the material with hierarchized and organized porosity for the preparation of said clear solution, or during said stage b) according to said first preferred embodiment of the process for preparation of the material with hierarchized and organized porosity or else during said stage d) and/or said stage e) according to said second preferred embodiment of the process for preparation of the material with hierarchized and organized porosity. The element X, preferably aluminum, can be introduced, several times, during the implementation of several stages according to all of the possible combinations of the embodiments that are described above. In particular, it is advantageous to introduce aluminum during said stage a) and said stage b) or during said stage a) and said stage d) and/or said stage e).

In the case where the element X is advantageously aluminum, amorphous aluminosilicate, obtained according to the process for preparation of the material with hierarchized and organized porosity, then exhibits an Si/Al molar ratio that is defined starting from the quantity of the silicon element that is introduced during stage a) of the process for preparation of the material with hierarchized and organized porosity and the total quantity of the aluminum element introduced in the stage(s) of the process for preparation of the material with hierarchized and organized porosity according to the different preferred embodiments described above. Under these conditions and in a preferred manner, the range of the Si/Al molar ratio of the material that is present in the catalyst that is used in the oligomerization process according to the invention is between 0.5 and 1,000.

When said first preferred embodiment of the process for preparation of the material with hierarchized and organized porosity is applied, the quantities of organic and inorganic material to be introduced for the implementation of stage b)

are to be adjusted based on the quantity of additional material of element X, advantageously of aluminum, introduced into stage b) according to said first method so that the total quantity of organic and inorganic material that is introduced for the preparation of the material that is present in the catalyst that is used in the process according to the invention made possible a phenomenon of micellization leading to the mesostructuring of the matrix of each particle of said material.

The amorphous material with hierarchized and organized porosity in the fields of microporosity and mesoporosity present in the catalyst that is used in the process according to the invention is obtained in powder form, which consists of elementary spherical particles that have a maximum diameter of 200 μm.

According to a first embodiment of the oligomerization process of the invention, the catalyst that is brought into contact with the olefinic hydrocarbon feedstock consists only of said amorphous material with hierarchized and organized porosity.

According to said first embodiment of the oligomerization process of the invention, said amorphous material with hierarchized and organized porosity that is obtained according to the preparation process described above in this description is then shaped and then finally subjected to a post-heat treatment stage, preferably a calcination stage. The calcination stage is usually implemented in air at a temperature of at least 150° C., preferably at least 250° C., and in a more preferred manner between approximately 350° C. and 1,000° C.

According to a second embodiment of the oligomerization process of the invention, the catalyst that is brought into contact with the olefinic hydrocarbon feedstock consists of said amorphous material with hierarchized and organized porosity and a binder. Said binder is a usually amorphous or poorly crystallized material, in general consisting of at least one refractory oxide in amorphous or poorly crystallized form. Said binder is generally selected from the group that is formed by alumina, silica, silica-alumina, clays, in particular natural clays such as kaolin or bentonite, magnesia, titanium oxide, boron oxide, zirconia, aluminum phosphates, titanium phosphates, zirconium phosphates, and carbon. The binder can also be selected from among the aluminates. In a preferred manner, the binder is an alumina in all of its forms that are known to one skilled in the art, and preferably gamma-alumina. The binder can also consist of a mixture of at least two of the oxides cited above, for example silica-alumina. In a preferred manner, binders that contain alumina, in all of the forms that are known to one skilled in the art, for example gamma-alumina, will be used. According to said second embodiment of the oligomerization process of the invention, the amorphous material with hierarchized and organized porosity is present in a quantity that ranges from 50 to 99.9% by weight of the catalyst and the binder in a quantity that ranges from 0.1 to 50% by weight of catalyst.

According to said second embodiment, said amorphous material with hierarchized and, organized, porosity that is obtained according to the process for preparation described above in this description is then shaped with a binder, and then finally subjected to a post-heat treatment stage, preferably a calcination stage. The calcination stage is usually implemented in air at a temperature of at least 150° C., preferably at least 250° C., and in a more preferred manner between approximately 350° C. and 1,000° C.

According to a third embodiment of the oligomerization process according to the invention, implemented in association with said first embodiment of the oligomerization process according to the invention or with said second embodiment of the oligomerization process according to the invention, the amorphous material with hierarchized and organized porosity, prepared according to the preparation process described above in this description, is subjected to at least one chemical treatment that is selected from among a treatment for bringing said material into contact with at least one metal and one treatment for neutralization of the acidity of the non-microporous surface of said material. The treatment for neutralization of the acidity of the non-microporous surface of said material is preferably implemented on the material that is not shaped and the chemical treatment that consists in bringing said material into contact with at least one metal can be implemented either before or after the shaping of said material.

According to said third embodiment of the oligomerization process according to the invention, a first chemical treatment to which is advantageously subjected said amorphous material with hierarchized and organized porosity is the bringing of said material into contact with at least one metal that is preferably selected from among the metals of groups IA, IIA, IIB, VIIB and VIII. The introduction of one or more metal(s), in particular in cationic form, is implemented by any technique that is known to one skilled in the art such as, for example, ion exchange, dry impregnation, excess impregnation, vapor phase deposition, etc. In a preferred manner, the introduction of one or more metal(s) is implemented by ion exchange(s). The ion exchange is generally implemented with a solution that contains a salt of the desired metal cation, in the manner known to one skilled in the art. The content by weight of metal(s) is advantageously between 0.01 and 10% by weight, and preferably between 0.05 and 5% by weight relative to the weight of the amorphous material with hierarchized and organized porosity.

According to said third embodiment of the oligomerization process according to the invention, a second chemical treatment to which said amorphous material with hierarchized and organized porosity is advantageously subjected is a treatment for neutralization of the acidity of the non-microporous surface of said amorphous material with hierarchized and organized porosity that is present in the catalyst that is used in the oligomerization process according to the invention. This treatment is also called selecting treatment. The partial neutralization of the acidity can be done by any method that is known to one skilled in the art. The conventional method that is generally employed for implementing the specific selection of the acid sites of a non-microporous surface is the adsorption of molecules whose kinetic diameter is greater than the diameter of the opening of the micropores of the amorphous material that is present in the oligomerization catalyst. The molecules that are generally used for passivating or selecting the non-microporous surface of the amorphous material that is present in the oligomerization catalyst are compounds that contain atoms that can interact with the sites of the non-microporous surface of the catalyst. In a preferred manner, the molecules that are used are organic or inorganic molecules that contain one or more silicon atom(s). In a very preferred manner, a molecular compound is involved that contains at least one silicon atom that is selected from among the compounds of formulas $Si-R_4$ and $Si_2-R_6$ where R can be either hydrogen, or an alkyl, aryl or acyl group, or an alkoxy (—OR') group, or a hydroxyl (—OH) group, or else a halogen, preferably an alkoxy (—OR') group. Within the same molecule $Si-R_4$ or $Si_2-R_6$, the group R can be either identical or different. For example, according to the formulas described above, it will be possible to select molecular compounds with the formula $Si_2H_6$ or $Si(C_2H_5)_3(CH_3)$. Thus, the molecular compound that contains at least of one silicon atom can be a compound such as silane, disilane, alkylsilane, alkoxysilane or siloxane. In a very preferred manner, said molecular compound exhibits a composition of general formula Si—(OR')$_4$ where R' is an alkyl, aryl or acyl group, preferably an alkyl group, and in a very preferred manner, an ethyl group. The implementation of said treatment for neutralization of the acidity of the non-microporous surface of the amorphous material that is present in the catalyst that is used in the process according to the invention is implemented by initiating the selecting of the non-macroporous surface of the amorphous material with hierarchized and organized porosity by gas phase deposition called CVD ("Chemical Vapor Deposition") deposition or a liquid phase deposition called CLD ("Chemical Liquid Deposition") deposition by any of the methods that are known to one skilled in the art. The selecting stage can be followed by a heat treatment that is implemented at a temperature that is preferably between 250 and 700° C., and preferably between 300 and 600° C. Said heat treatment stage is implemented in air, in oxygen, in hydrogen, in nitrogen or in argon, or in a mixture of nitrogen and argon, whereby said stage optionally can be implemented in the presence of water vapor. The period of this treatment is advantageously between 2 and 5 hours.

The shaping of the catalyst that is used in the oligomerization process according to the invention can be implemented, for example, by extrusion, by pelletizing, by the drop (oil-drop) coagulation method, by the rotating groove or drum method, by turntable granulation, or by any other method that is well known to one skilled in the art. In a preferred manner, the catalyst that is used in the oligomerization process according to the invention comes in the form of cylindrical or multilobed extrudates such as bilobed, trilobed, or multilobed extrudates of straight or twisted shape, but the catalyst can also optionally come in the form of crushed powders, tablets, rings, balls, and wheels. The shaping conditions of the catalyst, the selection of binder if it is present in the oligomerization catalyst, optionally the preliminary grinding of the material, the peptization process, the addition of pore-forming agents, the mixing time, the extrusion pressure if the catalyst according to the invention is put in the form of extrudates, and the speed and time of drying are determined according to the rules that are well known to one skilled in the art. In particular, for a shaping by extrusion, the latter is advantageously implemented by any conventional tool that is available commercially. The paste that is obtained from mixing is advantageously extruded through a die, for example using a piston or a single- or double-extrusion screw. This extrusion stage is advantageously implemented by any method that is known to one skilled in the art. In a very preferred manner, the catalyst that is used in the oligomerization process according to the invention comes in the form of extrudates with a diameter of between 0.5 and 5 mm, and more particularly between 0.7 and 2.5 mm. In a preferred manner, the cylindrical shape is used.

After shaping, the catalyst is subjected to a post-heat treatment stage, preferably a calcination stage, which is advantageously implemented in air at a temperature of at least 150° C., preferably at least 250° C., and in a more preferred manner between approximately 350° C. and 1,000° C.

Within the framework of the implementation of said second embodiment of the oligomerization process of the invention, the shaping stage of the catalyst that is used in the oligomerization process according to the invention is preferably preceded by a stage for bringing said material with hierarchized and organized porosity, prepared according to the preparation process described above, into contact with at least said binder. Said contact advantageously takes the form of powder, ground powder, a suspension or a suspension that has undergone a deagglomeration treatment. Thus, for example, the material with hierarchized and organized porosity can be put into suspension, which may or may not be slightly acidic, at a concentration that is adjusted to the final content of material with hierarchized and organized porosity targeted in the oligomerization catalyst. This suspension that is commonly called a slip is then mixed with the binder. This stage is implemented by any technique that is known to one skilled in the art.

The shaping of the catalyst that is used in the oligomerization process according to the invention is preferably implemented starting from the amorphous material with hierarchized and organized porosity that is obtained at the end of stage e) of the process for preparation of said material that is employed. However, said shaping can also be implemented starting from the amorphous material with hierarchized and organized porosity that is obtained at the end of stage d) of the process for preparation of said material that is employed, since the heat treatment stage, subsequent to the shaping stage, ensures the elimination of said structuring agent and of said surfactant that are used for the preparation of said amorphous material with hierarchized and organized porosity in the fields of microporosity and mesoporosity.

The process according to, the invention is a process for oligomerization of olefins that make possible the production of fuel, for example the production of gasoline and/or kerosene, starting from light olefinic feedstocks that contain between 2 and 10 carbon atoms per molecule, preferably between 2 and 8 carbon atoms per molecule, and in particular starting from light olefinic feedstocks that contain a large proportion of propylene and/or butenes and/or pentenes that use an oligomerization catalyst based on amorphous material with hierarchized and organized porosity described in this description.

The feedstock that is employed in the oligomerization process according to the invention contains 20% to 100% by weight, and preferably 25% to 80% by weight of olefins. The olefins that are present in the olefinic hydrocarbon feedstock can come from, for example, a catalytic cracking unit and/or a steam-cracking unit, and/or a unit for dehydrogenation of paraffins, and/or a unit for polymerizing dehydration of methanol in water and light olefins and/or any other sources that lead to the production of light olefins.

Impurities, such as, for example, water, sulfur derivatives, or basic nitrogen derivatives are preferably removed from the olefinic hydrocarbon feedstock that is sent into the oligomerization reactor that is used for the implementation of the oligomerization process of the invention, containing the catalyst that comprises said amorphous material with hierarchized and organized porosity, before the feedstock is introduced into the oligomerization reactor.

The olefinic hydrocarbon feedstock can be an olefinic C4 fraction, which usually comprises at most 90% by weight of isobutane, n-butane, 1-butene, 2-butenes, isobutene and optionally a small quantity of butadiene. The butadiene is generally eliminated upstream from the oligomerization by a selective hydrogenation process.

The olefinic hydrocarbon fraction can also be an olefinic C3-C4 fraction. The composition of the olefinic C3-C4 fraction is very variable according to its origin. It can comprise between approximately 20 and 50% by weight of propylene and propane, between approximately 50 and 80% by weight of isobutane, n-butane, 1-butene, 2-butenes, isobutene, and optionally a small quantity of butadiene. The butadiene is generally eliminated upstream from the oligomerization by a selective hydrogenation process.

The olefinic hydrocarbon feedstock can also be an olefinic C3 fraction. It usually comprises at least 90% by weight of propylene and propane.

The olefinic hydrocarbon feedstock can also be an olefinic C5 fraction. The composition of the olefinic C5 fraction is very variable according to its origin. It advantageously comprises between 30 and 80% of olefinic C5, between 1 and 20% by weight of olefinic C6, and between 1 and 20% by weight of olefinic C4.

According to the invention, the exothermicity of the oligomerization reaction can be managed by a recycling of at least a portion of the unconverted effluent, which contains in particular paraffins that have not been transformed during the reaction, to the oligomerization reactor, and/or by dilution of the feedstock by an addition of paraffins that come from another source, whereby said paraffins have the same molecular weight and/or are heavier than the olefinic feedstock, whereby said paraffins are aliphatic or cyclic.

In all of the cases of the processes that lead to the formation of gasoline and/or kerosene, and/or more generally an olefinic fraction with a boiling point that begins at a temperature of greater than 150° C., the olefinic fractions that are obtained at the output of the process optionally can be hydrogenated partially or totally.

Said oligomerization process is preferably implemented under the following operating conditions: the total pressure is between 0.1 and 20 MPa and preferably between 0.2 and 7 MPa, the temperature is between 30 and 600° C. and preferably between 40° C. and 400° C., and the hourly volumetric flow rate (VVH) is between 0.01 and 100 $h^{-1}$ and preferably between 0.05 and 20 $h^{-1}$.

According to the invention, the oligomerization process corresponds to an addition that is limited to essentially 2 to 6 basic monomers or molecules, whereby said monomers are olefins.

EMBODIMENTS OF THE OLIGOMERIZATION PROCESS OF THE INVENTION

First Embodiment

Selective Oligomerization

According to said first embodiment, an olefinic C4 fraction is brought into contact with the catalyst that comprises an amorphous material with hierarchized and organized porosity and that is prepared according to the process as described in this description so as to limit the overall conversion of the n-butenes to less than 10% by weight, and in a preferred manner to less than 5% by weight, whereas more than 90% by weight of the isobutene quantity, preferably more than 95% by weight, is converted. The isobutene is converted at more than 90% by weight into dimers and trimers. Then, the oligomerization effluent is subjected to a distillation such that one of the recovered fractions (light effluent) contains at most 90% by weight of butane, isobutane, and butenes that have not reacted during the oligomerization, at least one portion of this fraction then supplying, for example, an alkylation unit or a hydration unit, whereas the other fraction that consists of the oligomers that are obtained is used as a gasoline base, optionally after partial or total hydrogenation.

The embodiment of the oligomerization process described above corresponds to the embodiment called "selective oligomerization" in which the isobutene is converted for the most part.

According to said first embodiment of the oligomerization process of the invention, the oligomerization reaction is carried out at a temperature of between 30 and 300° C., under a pressure of between 0.1 and 20 MPa, and the volume of olefinic hydrocarbon feedstock that is sent per volume of catalyst and per hour is between 0.05 and 5 $h^{-1}$. Preferably, the temperature is between 40 and 160° C., and the pressure is between 2 and 7 MPa, so as to ensure that the reaction is carried out in liquid phase, or at least in homogeneous phase (i.e., entirely in liquid phase or entirely in gas phase), and the volume of olefinic hydrocarbon feedstock that is sent per volume of catalyst and per hour is preferably between 0.1 and 2.5 $h^{-1}$.

The technology of the oligomerization reactor can be a fixed bed, a fluidized bed, or a circulating bed. The preferred technology is a fixed-bed implementation.

In a preferred manner, the thus obtained oligomers are reinjected into an additional oligomerization reactor that contains, for example, the oligomerization catalyst that comprises amorphous material with hierarchized and organized porosity as described above, so as to increase the chain length of the oligomers and thus to attain the kerosene fraction, or more generally an olefinic fraction, with a boiling point that begins at a temperature of greater than 150° C.

In an advantageous manner, the light oligomerization effluent, i.e., the C4 fraction, can be introduced into a hydroisomerization reactor whose purpose is to hydroisomerize a portion of the unconverted 1-butene into 2-butene so as to draw closer to the thermodynamic balance. The other components of the effluent then are not converted significantly during the hydroisomerization stage. The conversion of 1-butene into 2-butene is very useful if the thus obtained C4 fraction at the output of the hydroisomerization reactor can then be introduced into an aliphatic alkylation reactor on hydrofluoric acid, the products obtained by alkylation of the 2-butene with isobutane having a better octane number than the alkylate that is obtained starting from 1-butene.

Given the strong exothermicity of the oligomerization reaction, the quantity of isobutene in the hydrocarbon feedstock that supplies the oligomerization reactor is preferably less than 35% by weight, and in an even more preferred manner less than 15% by weight, whereby said quantity is optionally obtained by diluting the feedstock, for example with butane or isobutane or the raffinate of the oligomerization unit.

Second Embodiment

According to said second embodiment, an olefinic C4 fraction or an olefinic C3-C4 fraction is brought into contact with the oligomerization catalyst that comprises at least one amorphous material with hierarchized and organized porosity as described in this description such that a portion of the butenes contained in the hydrocarbon feedstock is converted into dimers or trimers, and then used as a gasoline base. According to said second embodiment of the process of the invention, less than 80% by weight of the butenes is converted, and at least 80% by weight, preferably at least 90% by weight, of the isobutene is converted. This process makes it possible to produce a maximum quantity of gasoline while minimizing the quantity of kerosene that is formed.

In the oligomerization reactor that is used for the implementation of said second embodiment, the temperature is between 40 and 250° C., preferably between 50 and 200° C., and the pressure is between 0.1 and 10 MPa, preferably between 0.1 and 6 MPa, and the quantity of hydrocarbon feedstock that is sent per volume of catalyst and per hour is between 0.05 and 5 $h^{-1}$, preferably between 0.1 and 2.5 $h^{-1}$.

The technology of the reactor can be a fixed bed, a fluidized bed, or a circulating bed. The preferred technology implements a fixed bed.

A variant of said second embodiment of the process of the invention consists in using as a feedstock an olefinic feedstock in which the isobutene was first eliminated partially or totally, for example by using an etherification unit upstream from the oligomerization unit by selectively reacting the isobutene with an alcohol, for example methanol or ethanol, without converting the n-butene, or else by using a selective oligomerization unit, such as the one described above in said first embodiment, upstream from the oligomerization unit. The oligomers that are produced then have fewer branches than those obtained by treatment of the complete fraction including the isobutene.

Third Embodiment

A third embodiment of the process according to the invention consists in subjecting an olefinic C4 fraction, optionally containing traces of propylene, to an oligomerization such that the major portion of the butenes contained in the feedstock is converted into dimers or trimers, and then used as a gasoline base. According to said third embodiment of the process of the invention, at least 90% by weight of 1-butene, at least 80% by weight of 2-butenes, at least 97% by weight of isobutene and at least 80% by weight of propylene are converted. Said third embodiment of the process of the invention makes it possible to produce a maximum quantity of gasoline without manufacturing kerosene. The olefinic C4 fraction usually comprises isobutane, n-butane, 1-butene, 2-butene, isobutene and optionally a small quantity of butadiene. The butadiene is generally eliminated upstream from the oligomerization by a selective hydrogenation process to prevent polymerization reactions that would make the catalyst inactive.

Said process that is implemented according to said third embodiment comprises the following stages:

A first oligomerization stage: an olefinic C4 fraction is treated in a first oligomerization reactor in which the overall conversion of n-butenes contained in the feedstock is less than 45% by weight, and the conversion of the isobutene is greater than 80% by weight, preferably greater than 85% by weight, whereby the oligomers that are obtained are dimers and trimers with more than 80% by weight, The effluent of the first oligomerization stage is sent into a fractionation column so as to recover a first fraction that contains isobutene and unconverted n-butenes and a second fraction that consists in 90% by weight of dimers and trimers of the oligomerization reaction, A second oligomerization stage: said first recovered fraction is introduced into a second oligomerization reactor in which the olefins are converted in large part into dimers and trimers, i.e., at least 50% by weight of the n-butenes is converted, preferably at least 75% by weight of 1-butene and at least 55% by weight of 2-butene are converted, and The effluent of the second oligomerization stage is sent into the fractionation column that is combined with the first oligomerization reactor, or into a second column for separating the gasoline or the kerosene from unconverted C4 compounds.

In the oligomerization reactors, the temperature is between 40 and 250° C., preferably between 45 and 200° C., and the pressure is between 0.1 and 10 MPa, preferably between 0.1 and 6 MPa, and the quantity of hydrocarbon feedstock that is sent per volume of catalyst and per hour is between 0.05 and 5 preferably between 0.1 and 2.5 $h^{-1}$. The technology of the reactor can be a fixed bed, a fluidized bed, or a circulating bed. Preferably, the technology is a fixed bed.

Preferably, in the second oligomerization reactor, the operating conditions are more strict than in the first reactor.

Said third embodiment of the process of the invention can be applied to an olefinic C3-C4 feedstock.

Fourth Embodiment

According to said fourth embodiment, an olefinic C4 fraction or an olefinic C3-C4 fraction is brought into contact with the oligomerization catalyst that comprises the amorphous material with hierarchized and organized porosity as described in this description such that the major portion of the butenes contained in the feedstock is converted, so as to form a gasoline base and a kerosene base. According to said fourth embodiment of the process of the invention, at least 90% by weight of the 1-butenes, at least 80% by weight of 2-butenes, and at least 97% by weight of the isobutene are converted. The olefinic C4 fraction usually essentially comprises isobutane, n-butane, 1-butene, 2-butene, isobutene and optionally a small quantity of butadiene. The olefinic C3-C4 fraction in addition comprises propane and propylene in the proportions given above in this description.

In the oligomerization reactor, the temperature is between 60 and 250° C., preferably between 100 and 200° C., and the pressure is between 0.1 and 10 MPa, preferably between 0.1 and 6 MPa, and the quantity of hydrocarbon feedstock that is sent per volume of catalyst and per hour is between 0.05 and 5 $h^{-1}$, preferably between 1 and 2.5 $h^{-1}$. The technology of the reactor can be a fixed bed, a fluidized bed, or a circulating bed. Preferably, the technology is a fixed bed.

Fifth Embodiment

According to said fifth embodiment, an olefinic C3 fraction is brought into contact with said oligomerization catalyst that comprises the amorphous material with hierarchized and organized porosity that is described in this description such that the major portion of the propylene that is contained in the feedstock is converted, i.e., that at least 80% by weight of the propylene that is contained in the feedstock is converted so as to form a gasoline base and a kerosene base. The olefinic C3 fraction usually comprises at least 90% by weight of propylene and propane.

The oligomerization reaction is carried out at a temperature of between 30 and 300° C., under a pressure of between approximately 0.1 and 20 MPa, and the volume of hydrocarbon feedstock that is sent per volume of catalyst and per hour is between 0.05 and 5 $h^{-1}$. Preferably, the temperature is between 40 and 160° C., and the pressure is between 2 and 7 MPa, and the volume of hydrocarbon feedstock that is sent per volume of catalyst and per hour is preferably between 0.1 and 2.5 $h^{-1}$. The technology of the reactor can be a fixed bed, a fluidized bed, or a circulating bed. The preferred technology is a fixed-bed implementation.

The following examples illustrate this invention without limiting its scope.

EXAMPLES

In the following examples, the aerosol technique that is used is the one that is described above in the disclosure of the invention: a model 9306 A aerosol generator that has a 6-jet atomizer provided by TSI is used.

For the materials M1 and M2 shown below, the ratio $V_{inorganic}/V_{organic}$ of the mixture that is obtained from stage b) is calculated. This ratio is defined as follows: $V_{inorganic}/V_{organic} = (m_{inorg}*\rho_{org})/(m_{org}*\rho_{inorg})$ where $m_{inorg}$ is the final mass of the inorganic fraction in the form of condensed oxides, namely $SiO_2$ and $AlO_2$, in the solid elementary particle that is obtained by atomization; $m_{org}$ is the total mass of the non-volatile organic fraction that is found in the solid elementary particle that is obtained by atomization, namely the surfactant and the structuring agent; $\rho_{org}$ and $\rho_{inorg}$ are the densities that are respectively combined with non-volatile organic and inorganic fractions. In the following examples, it is considered that $\rho_{org}=1$ and $\rho_{inorg}=2$. Also, the ratio $V_{inorganic}/V_{organic}$ is calculated as being equal to $V_{inorganic}/V_{organic} = (m_{SiO2}+m_{AlO2})/[2*(m_{structuring\ agent}+m_{surfactant})]$. Ethanol, soda, and water do not come into play in the calculation of said ratio $V_{inorganic}/V_{organic}$.

Example 1

Preparation of a Material M1 with Hierarchized Porosity in the Fields of Microporosity and Mesoporosity and with Organized Porosity in the Field of Mesoporosity Whose Microporous Amorphous Walls Consist of ZSM-5-Type (MFI) Aluminosilicate Protozeolitic Entities Such that the Si/Al Molar Ratio=49

6.86 g of a tetrapropylammonium hydroxide solution (TPAOH 40% by mass in an aqueous solution) is added to 0.37 g of aluminum sec-butoxide $(Al(O^sC_4H_9)_3)$. After 30 minutes of vigorous stirring at ambient temperature, 27 g of demineralized water and 18.75 g of tetraethylorthosilicate (TEOS) are added. The whole mixture is left under vigorous stirring at ambient temperature for 18 hours so as to obtain a clear solution. A solution that contains 66.61 g of ethanol, 61.24 g of water, and 5.73 g of surfactant F127 (pH of the mixture 13.5) is then added to this solution. The ratio $V_{inorganic}/V_{organic}$ of the mixture is equal to 0.32. The whole mixture is left under stirring for 10 minutes. The mass is sent into the atomization chamber of the aerosol generator as it has been described in the description above, and the solution is sprayed in the form of fine droplets under the action of carrier gas (dry air) introduced under pressure (P=1.5 bar). The droplets are dried according to the protocol that is described in the disclosure of the invention above: they are conveyed via an $O_2/N_2$ mixture into PVC pipes. They are then introduced into a furnace that is adjusted to a drying temperature set at 350° C. The collected powder is then dried for 18 hours in the oven at 95° C. The solid is characterized by low-angle XRD, by nitrogen volumetric analysis, by TEM, by SEM, and by XF. The TEM analysis shows that the final material has an organized mesoporosity that is characterized by a vermicular structure. The analysis by nitrogen volumetric analysis combined with the analysis by the method c' leads to a value of the micropore volume $V_{micro}$ $(N_2)$ of 0.13 ml/g, a value of the mesopore volume $V_{meso}$ $(N_2)$ of 0.61 ml/g, and a specific surface area of the final material of S=781 m²/g. The mesopore diameter $\phi$ that is characteristic of the mesostructured matrix is 7 nm. The small-angle XRD analysis leads to the display of a correlation peak at the angle $2\theta=0.78°$ Bragg's equation $2d*\sin(\theta)=1.5406$ makes it possible to calculate the distance d for correlation between the organized mesopores of the material, or d 11.3 nm. The thickness of the walls of the mesostructured material defined by $e=d-\phi$ is therefore e=4.3 nm. The Si/Al molar ratio that is obtained by XF is 49. A SEM picture of the thus obtained spherical elementary particles indicates that these particles have a size that is characterized by a diameter that varies from 50 to 3,000 nm, whereby the size distribution of these particles is centered around 300 nm.

The material M1 is thus obtained.

Example 2

Preparation of a Material M2 with Hierarchized Porosity in the Fields of Microporosity and Mesoporosity and Organized Porosity in the Field of Mesoporosity Whose Microporous Amorphous Walls Consist of ZSM-5-Type (MFI) Aluminosilicate Protozeolitic Entities Such that the Si/Al Molar Ratio=12

6.86 g of a solution of tetrapropylammonium hydroxide (TPAOH 40% by mass in an aqueous solution) is added to 1.71 g of aluminum sec-butoxide $(Al(O^sC_4H_9)_3)$. After 30 minutes of vigorous stirring at ambient temperature, 27 g of demineralized water and 17.66 g of tetraethylorthosilicate (TEOS) are added. The whole mixture is left under vigorous stirring at ambient temperature for 4 days so as to obtain a clear solution. A solution that contains 66.61 g of ethanol, 61.24 g of water, and 5.73 g of surfactant F127 (pH of the mixture=12) is then added to this solution. The ratio $V_{inorganic}/V_{organic}$ of the mixture is equal to 0.32 and is calculated as described above. The whole mixture is left under stirring for 10 minutes. The mass is sent into the atomization chamber of the aerosol generator as it has been described in the description above, and the solution is sprayed in the form of fine droplets under the action of carrier gas (dry air) that is introduced under pressure (P=1.5 bar). The droplets are dried according to the protocol that is described in the disclosure of the invention above: they are conveyed via an $O_2/N_2$ mixture into PVC pipes. They are then introduced into a furnace that is adjusted to a drying temperature set at 350° C. The collected powder is then dried for 18 hours in the oven at 95° C. The solid is characterized by low-angle XRD, by nitrogen volumetric analysis, by TEM, by SEM, and by XF. The TEM analysis shows that the final material has an organized mesoporosity that is characterized by a vermicular structure. The analysis by nitrogen volumetric analysis combined with the analysis by the method $\alpha_s$ leads to a value of the micropore volume $V_{micro}$ $(N_2)$ of 0.03 ml/g, a value of the mesopore volume $V_{meso}$ $(N_2)$ of 0.45 ml/g, and a specific surface area of the final material of S=595 m²/g. The mesopore diameter $\phi$ that is characteristic of the mesostructured matrix is 5 nm. The small-angle XRD analysis leads to the display of a diffraction peak at the angle $2\theta=0.98°$. Bragg's equation $2d*\sin(\theta)=1.5406$ makes it possible to calculate the distance d for correlation between the organized mesopores of the material, or d=9 nm. The thickness of the walls of the mesostructured material defined by $e=d-\phi$ is therefore e=4 nm. The Si/Al molar ratio that is obtained by XF is 12. A SEM picture of the thus obtained spherical elementary particles indicates that these particles have a size that is characterized by a diameter that varies from 50 to 3,000 nm, whereby the size distribution of these particles is centered around 300 nm.

The material M2 is thus obtained.

Example 3

Preparation of the Catalysts C1 and C2

The materials M1 and M2 that are prepared in Examples 1 and 2 are obtained in powder form. They are then shaped by extrusion. The extrudates that are obtained are cylindrical with a diameter of 1.6 mm. The latter are then dried at 120° C. and then calcined in air for 5 hours at 550° C. The catalysts C1 and C2 are thus obtained.

Example 4

Catalytic Evaluation of the Catalysts C1 and C2

An olefinic C4 fraction that is obtained from a catalytic cracking unit is dried on 3A/13X-type molecular sieves to eliminate the traces of sulfur and water. The composition of the feedstock at the end of these treatments is recorded in Table 1. This feedstock is used to execute the oligomerization tests in the presence of the C1 and C2 catalysts.

TABLE 1

Composition of the Oligomerization Feedstock of Light Olefins.

| Composition of the Feedstock | (% by Weight) |
|---|---|
| Isobutane | 30.4 |
| n-Butane | 11.1 |
| Isobutene | 12.0 |
| 1-Butene | 15.2 |
| 2-Butenes | 31.3 |

The C1 and C2 catalysts are successively loaded into a fixed-bed reactor and tested for the oligomerization reaction of the feedstock described in Table 1. The operating conditions that are applied in the oligomerization reactor are such that the pressure is equal to 5.5 MPa and the VVH (volume of catalyst/volumetric flow rate of feedstock) is equal to 1 $h^{-1}$. The catalysts are activated in situ before the oligomerization reaction under $N_2$ at 250° C. for 2 hours. Each catalyst is tested at two temperatures: first at 70° C. and then at 160° C.

The conversions of the olefins by the C1 and C2 catalysts at oligomerization temperatures of 70° C. and 160° C. that are under study, and more particularly the conversions of isobutene and n-butenes, namely 1-butene and 2-butenes, are recorded in Table 2. The conversion is defined as the ratio between the quantity of converted olefins and the total quantity of olefins initially present in the feedstock.

The yield of C8+ oligomers is defined as the mass of oligomers that is produced comprising at least 8 carbon atoms divided by the mass of oligomers that is produced comprising at least 8 carbon atoms obtained for a total conversion of the olefinic feedstock.

TABLE 2

Performance Levels of the Catalysts C1 and C2.

| | Catalyst | | | |
|---|---|---|---|---|
| | C1 | | C2 | |
| Temperature | 70° C. | 160° C. | 70° C. | 160° C. |
| Conversion of n-Butenes (% by Weight) | 26.3 | 75.2 | 28.2 | 73.5 |
| Conversion of Isobutene (% by Weight) | 100 | 100 | 100 | 100 |
| Yield of C8+ (% by Weight) | 41.0 | 79.0 | 42.6 | 77.0 |

The C1 and C2 catalysts are very active catalysts for the oligomerization reaction of the olefinic C4 feedstock. Actually, at 70° C. and 160° C., the conversion of the isobutene of the feedstock is at maximum (100%). The conversion of the normal butenes increases with the temperature for reaching a high value at 160° C.

The invention claimed is:

1. A process for oligomerization of an olefinic feedstock containing olefinic hydrocarbon molecules having 2 to 10 carbon atoms per molecule, said process comprising bringing said olefinic feedstock into contact with a catalyst comprising at least one amorphous material having hierarchized and organized porosity and including at least two elementary spherical particles, wherein each of said particles comprises a mesostructured silicon-oxide-based matrix having a uniform diameter of mesopores of between 1.5 and 30 nm and having amorphous and microporous walls with a thickness of between 1 and 50 nm, said elementary spherical particles having a maximum diameter of 200 microns, said amorphous walls consisting of protozeolitic entities and the preparation of said catalyst comprising:
   a) preparing a clear solution that contains precursor elements of protozeolitic entities, wherein said precursor elements are at least one structuring agent, at least one silicic precursor, and at least one precursor of at least one element X;
   wherein the element X is aluminum, iron, germanium, titanium, or boron;
   wherein the reaction mixture is aqueous or aqua-organic;
   wherein the structuring agent is basic or the reaction medium additionally includes alkaline metal hydroxide;
   wherein said reaction mixture is treated under hydrothermal conditions under autogenous pressure at a temperature between ambient temperature and 200° C. until the formation of a clear solution;
   b) mixing at least one surfactant and at least said clear solution that is obtained according to a) in a solution wherein the ratio of the volumes of inorganic and organic materials is between 0.26 and 4, wherein said solution has a pH that is greater than 9;
   c) atomizing said solution that is obtained in stage b) by generating an aerosol and forming spherical droplets of said solution;
   d) drying said droplets; and
   e) eliminating said structuring agent and said surfactant for obtaining an amorphous material with hierarchized porosity in the range of microporosity and mesoporosity and organized within the range of mesoporosity.

2. Oligomerization process according to claim 1, such that said catalyst comprises at least one binder that is selected from the group that is formed by alumina, silica, silica-alumina, clays, magnesia, titanium oxide, boron oxide, zirconia, aluminum phosphates, titanium phosphates, zirconium phosphates, and carbon.

3. Oligomerization process according to claim 1, such that said catalyst comprises at least one metal that is selected from among the metals of groups IA, IIA, IIB, VIIB and VIII.

4. Oligomerization process according to claim 1, such that said catalyst in the form of extrudates with a diameter of between 0.5 and 5 mm.

5. Oligomerization process according to claim 1, such that the diameter of the mesopores of said material that is present in said catalyst is between 4 and 30 nm.

6. Oligomerization process according to claim 1, such that said protozeolitic entities are radicals for initiating at least one zeolite that is selected from the group consisting of TON-, MTT-, BEA-, MFS-, MFI-, MOR- and FER-structural zeolites.

7. Oligomerization process according to claim 1, such that said silicon-oxide-based matrix that forms each of the elementary spherical particles of said material that is present in said catalyst comprises at least one element X that is selected from among aluminum, iron, germanium, titanium and boron.

8. Oligomerization process according to claim 7, such that the element X is aluminum.

9. Oligomerization process according to claim 1, such that said olefinic feedstock contains olefinic hydrocarbon molecules that have 2 to 8 carbon atoms per molecule.

10. Oligomerization process according to claim 1, such that said olefinic feedstock is an olefinic C3 fraction that comprises at least 90% by weight of propylene and propane.

11. Oligomerization process according to claim 1, such that said olefinic feedstock is an olefinic C3-C4 fraction.

12. Oligomerization process according to claim 1, such that said olefinic feedstock is an olefinic C4 fraction that comprises at most 90% by weight of isobutane, n-butane, 1-butene, 2-butenes, and isobutene.

13. Oligomerization process according to claim 1, such that said olefinic feedstock is an olefinic C5 fraction.

14. Oligomerization process according to claim 1, such that it is implemented under the following operating conditions: the total pressure is between 0.1 and 20 MPa, and the temperature is between 30 and 600° C.; the hourly volumetric flow rate (VVH) is between 0.01 and 100 $h^{-1}$.

15. Oligomerization process according to claim 1, said reaction mixture is put under hydrothermal conditions under autogenous pressure at a temperature between ambient temperature and 170° C.

* * * * *

UNITED STATES PATENT AND TRADEMARK OFFICE
CERTIFICATE OF CORRECTION

PATENT NO.        : 8,742,193 B2                                        Page 1 of 1
APPLICATION NO.   : 12/994213
DATED             : June 3, 2014
INVENTOR(S)       : Amandine Cabiac et al.

It is certified that error appears in the above-identified patent and that said Letters Patent is hereby corrected as shown below:

Title page, Item [12] and Item [75] (Inventors): reads "Amandine Cabias", should read --Amandine Cabiac--;

In the Claims

Column 30, line 55, claim 4, reads "said catalyst in the form of extrudates with a diameter of", should read --said catalyst comes in the form of extrudates with a diameter of--.

Signed and Sealed this
Fifth Day of May, 2015

Michelle K. Lee
*Director of the United States Patent and Trademark Office*